US006207134B1

(12) United States Patent
Fahlvik et al.

(10) Patent No.: US 6,207,134 B1
(45) Date of Patent: Mar. 27, 2001

(54) ULTRAFINE LIGHTLY COATED SUPERPARAMAGNETIC PARTICLES FOR MRI

(75) Inventors: Anne Kjersti Fahlvik; Anne Nævestad; Helge Gundersen; Per Strande; Jo Klaveness, all of Oslo; Anne Jacobsen, Bærums Verk, all of (NO)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 09/243,437

(22) Filed: Feb. 3, 1999

Related U.S. Application Data

(63) Continuation of application No. 08/809,291, filed as application No. PCT/GB94/02097 on Sep. 27, 1994, now abandoned.

(51) Int. Cl.[7] .................................................. A61B 5/055
(52) U.S. Cl. .......................................................... 424/9.322
(58) Field of Search ........................ 424/9.322; 600/420

(56) References Cited

U.S. PATENT DOCUMENTS

| 4,770,183 | * | 9/1988 | Groman et al. | 424/9.32 |
|---|---|---|---|---|
| 5,055,288 | * | 10/1991 | Lewis et al. | 424/9.32 |
| 5,204,457 | * | 4/1993 | Maruno et al. | 536/101 |
| 5,225,282 | * | 7/1993 | Chagnon et al. | 428/407 |
| 5,284,646 | * | 2/1994 | Menz et al. | 424/9.322 |
| 5,314,679 | * | 5/1994 | Lewis et al. | 424/9.322 |
| 5,368,840 | * | 11/1994 | Unger | 424/9 |
| 5,411,730 | * | 5/1995 | Kirpotin et al. | 424/9.322 |
| 5,424,419 | * | 6/1995 | Hasegawa et al. | 536/113 |
| 5,427,767 | * | 6/1995 | Kresse et al. | 424/9.32 |
| 5,679,323 | * | 10/1997 | Menz et al. | 424/9.322 |
| 5,746,999 | * | 5/1998 | Gries et al. | 424/9.322 |
| 5,766,572 | * | 6/1998 | Hasegawa et al. | 424/9.322 |

FOREIGN PATENT DOCUMENTS

| 0 516 252 | 12/1992 | (EP) . |
|---|---|---|
| 0 580 878 | 2/1994 | (EP) . |
| 91 05807 | 5/1991 | (WO) . |
| 91 15753 | 10/1991 | (WO) . |
| 94 03501 | 2/1994 | (WO) . |
| 94/03501 * | 2/1994 | (WO) . |

OTHER PUBLICATIONS

Colet et al., "Effect of opsonins on the uptake of magentic starch microspheres by rat Kupffer cells" Database CHEM-ABS, Chemical Abstracts Service, Columbus, Ohio, U.S., AN=122:127676, 1994.

Bodmeier et al., "A novel approach to the oral delivery of micro–or nanoparticles," DATABASE CHEMABS, Chemical Abstracts Service, Columbus, Ohio, U.S., 1989.

Yeh et al., Magnetic Resonance in Medicine, vol. 30, No. 5 Nov., 1993, pp. 617–625.

* cited by examiner

Primary Examiner—Gary E. Hollinden
(74) Attorney, Agent, or Firm—Bacon & Thomas (57) ABSTRACT

The invention relates to particulate contrast agents, especially contrast agents for MR imaging having a metal oxide core which is preferably superparamagnetic iron oxide. The particulate contrast agents are provided with a low coating density of a polyelectrolyte coating agent selected from structural polysaccharides and synthetic polymers, especially polyaminoacids. Unlike conventional coated particulates, the new particles have reduced or no effect on cardiovascular parameters, platelet depletion, complement activation and blood coagulation.

15 Claims, 3 Drawing Sheets

ULTRAFINE LIGHTLY COATED SUPERPARAMAGNETIC PARTICLES FOR MRI

This application is a continuation application of U.S. appplication Ser. No. 08/809,291 filed Sep. 2, 1997, now abandoned which is the national phase of international application number PCT/GB94/02097 filed Sep. 27, 1994.

BACKGROUND OF THE INVENTION

1. Field of the Invention

The present invention is directed to contrast agents, in particular, polyelectrolyte coated metal oxide contrast agent particles for use in MR, X-ray, EIT and magnetometric studies, especially where such metal oxide particles exhibit superparamagnetic behaviour.

2. Background of the Information

The use of contrast agents in medical diagnostic techniques to enhance tissue contrast or to facilitate the study of body processes is well established. The manner in which contrast enhancement occurs varies from imaging modality to imaging modality but in magnetic resonance imaging most of the conventional contrast agents derive their contrast enhancing power from their effects on the tissue selection times.

One of the great advantages of MR imaging is the high degree of intrinsic tissue contrast present from tissue relaxations times. The initial belief was that even without added contrast agents the relaxation parameters could be used for discrimination between normal and malignant tissue (see Damadian, Science 171:1151–1153 (1971)). However, it has become clear since the first MR images were produced by Lauterbur (see Nature 242:190–191 (1973)) that a consistent differentiation of abnormal tissue from normal was impossible. Therefore, there has for some time now been great interest in the use of materials which improve contrast by affecting the key contrast parameters. Lauterbur's group was first to describe the use of MR contrast agents in animals (see Lauterbur et al., Frontiers of Biological Energetics, New York, Academic Press 1978; page 752). The clinical diagnostic potential of an intravenously administered contrast agent was demonstrated by Carr et al. in 1984 (see Carr et al., AJR 143:215–224 (1984)) and the first MR contrast agent, GdDTPA, received approval for clinical use in 1988.

Today it is well documented that GdDTPA and similar substances, like GdDTPA-BMA, GdHPDO3A and GdDOTA, are safe and beneficial for enhanced MR imaging of the central nervous system. Due to their low molecular weight and hydrophilic properties, these metal chelates distribute extracellularly and are rapidly cleared by the kidney. Currently, other contrast agents are being developed with improved pharmacokinetic properties, allowing a more specific organ or disease distribution.

There are, generally speaking, two approaches that may be used to improve the delivery of a MR contrast agent to the target region. In the conventional one, efforts are directed towards using paramagnetically labelled naturally occurring or synthetic molecules or macromolecules with a specific accumulation or localization (e.g. hepatobiliary agents, blood pool agents, porphyrins). An alternative is to use stronger magnetic labels, such as superparamagnetic particles, which accumulate in the desired site by virtue of their particulate nature or by use of their binding to target specific molecules. In general, the diagnostically profitable target/background ratios of the superparamagnetic agents are significantly higher than those of the paramagnetic agents and the superparamagnetic agents can therefore be detected at very low tissue concentrations (see Weissleder et al., Magn. Reson. Quart 8:55–63 (1992)).

The application as MR contrast agents of superparamagnetic agents derives from their ideal combination of a large effect on tissue signal intensity which results in powerful contrast enhancement, and their highly specific targetability. The potential targets of particulate agents are many, depending on the administration route and the physicochemical properties of the particulate material, in particular the particle size and surface characteristics. Their two main applications are by enteral administration for gastrointestinal investigations, and by parenteral administration for investigations of the blood pool compartment and/or the reticuloendothelial system and regions of its anatomical distribution, e.g. the liver, spleen, bone marrow, and lymph nodes. Ultrasmall iron oxide particles with a diameter of less than approximately 30 nm have a relatively long intravascular half life when compared to larger conventional iron oxide particles. In addition to the T2 shortening typically associated with the iron oxide particles, ultrasmall particles also produce T1 shortening thereby increasing signal within the vessels. Recent advances in particulate agents have also made targeting with receptor ligands or antibodies/antibody fragments possible. A brief summary of described applications of different superparamagnetic agents is given in Fahlvik et al., JMRI 3:187–194 (1993).

Up to the present, much of the work carried out in superparamagnetic contrast agents has focused on optimizing their contrast efficiency and biokinetics. Little attention has been paid to pharmaceutical formulation related issues or to safety aspects of the particle preparations.

However for parenteral particulate preparations, adequate contrast efficacy and biokinetics are not in themselves sufficient and certain problems have been encountered. Thus, for example, the conventional iron oxide-dextran preparation, which has been tested in clinical trials, has been shown to have a low colloidal stability. The particles must be redispersed and/or diluted and filtered immediately before use and the preparation is administered as a slow infusion through an in-line filter to avoid severe toxic effects.

While particulates can be coated to give adequate stability, the particle surface area of a parenteral particulate agent is substantial and we have found that coating agents conventionally thought to be wholly innocuous, such as for example the storage-type polysaccharides starch and dextran and their derivatives can themselves have a deleterious effect on cardiovascular parameters, platelet depletion, blood coagulation time and on the complement system.

SUMMARY OF THE INVENTION

We have however found that these problems with particulate agents may be avoided or reduced by the use of lower than conventional coating densities of certain polyelectrolyte coating materials such as synthetic polyaminoacids, synthetic polymers and, especially, structural-type polysaccharides.

Thus viewed from one aspect the invention provides a diagnostic agent comprising a composite particulate material the particles whereof comprise a diagnostically effective, substantially water-insoluble, metal oxide crystalline material and a polyionic coating agent, wherein said particles have a size of below 300 nm, said crystalline material has a crystal size of from 1 to 100 nm, the weight ratio of said crystalline material to said coating agent is in the range 1000:1 to 11:1, and said coating agent is selected from the group consisting of natural and synthetic structural-type polysaccharides, synthetic polyaminoacids, physiologically tolerable synthetic polymers and derivatives thereof.

Polysaccharides are widely found in nature and can generally be split into the two categories of storage-type polysaccharides (such as starch, glycogen, dextran and derivatives thereof) and the structural polysaccharides such as pectins and pectin fragments such as polygalacturonic acid, the glycosaminoglycans and heparinoids (e.g. heparin, heparan, keratan, dermatan, chondroitin and hyaluronic acid), celluloses and the marine polysaccharides such as alginates, carrageenans and chitosans, and their derivatives.

The present invention is concerned with the second category, and with both natural and synthetic forms of these polysaccharides, including such polysaccharides which have been fragmented or chemically modified, eg derivatised to introduce attachment sites for binding to the metal oxide crystals.

Particularly preferred as the polyionic polysaccharides coating agents are the natural and synthetic heparinoid polysaccharides, such as heparins, chrondroitins (e.g. chrondroitin-4-sulphate), and the marine polysaccharides alginates, carrageenans and chitosans.

Less preferably, synthetic polyionic polymers, eg polyaminoacids, polyacrylates, and polystyrenesulphonates (and other synthetic polymers as mentioned in EP-A-580818) may be used as coating agents. Among the polyaminoacids homo and copolymers of lysine, glutamic acid and aspartic acid and their esters (eg methyl and ethyl esters) are preferred.

In general, the coating agent should contain a multiplicity of ionic groups, e.g. amine, carboxy, sulphate, sulphonate, phosphonate or phosphate groups, spaced along the polymer to allow multiple points of attachment to the metal oxide crystal surface as well as to provide the composite particle as a whole with a net electrical charge, preferably negative, which is measurable as a zeta potential. The multiple attachment ensures a firm autoclave-resistant binding and storage stability while the net charge assists in enhancing the biotolerability of the particle following administration into the vasculature.

Generally the polyionic coating agent will have a molecular weight in the range 500 to 2000000 D, more especially 1000 to 500000, particularly 1500 to 250000, more particularly 2000 to 150000 D.

The surface bound coating agent makes up a small portion of the overall composite particle, the weight ratio of crystalline material to coating agent preferably lying in the range 1000:1 to 15:1, especially 500:1 to 20:1, particularly 100:1 to 25:1, more particularly at least 20:1 for heparin or chondroitin coatings.

Composite particle production will generally be effected in a one or two stage coating procedure In the one stage procedure the crystalline material is formed by precipitation at high pH (eg above 9, preferably above 11) with a base in the presence of the coating agent while in the two stage procedure the crystalline material is formed first and then coated.

Thus viewed from a further aspect the invention provides a process for producing the contrast agent of the invention, said process comprising:

(i) at a pH above 9, co-precipitating 1 to 100 nm crystals of a diagnostically effective substantially water-insoluble metal oxide and a coating agent
or (ii) coating 1 to 100 nm crystals of a diagnostically effective substantially water-insoluble metal oxide with a coating agent whereby to yield a composite particle having a size below 300 nm and a crystal to surface bound coating agent weight ratio of 1000:1 to 11:1, said coating agent being selected from the group consisting of natural and synthetic structural-type polysaccharides and derivatives thereof, synthetic polyaminoacids and physiologically tolerable synthetic polymers, preferably however said coating agent being a structural-type polysaccharide.

The procedures for co-precipitation or post-precipitation coating are well known and widely described in the literature as described below (see for example U.S. Pat. No. 4,795,698 and U.S. Pat. No. 4,452,773).

As not all the coating agent is deposited, it may be necessary to use a 1½ to 7, generally about 2-fold excess (relative to the amount needed if coating binding was 100%) to achieve the desired coating density.

The nature of the crystalline material in the compositions of the invention will of course depend on its intended function. While the invention is applicable generally to all substantially insoluble crystalline materials for which parenteral administration followed by target specific delivery or extended blood pool residence is desired, it is however especially applicable to the case of metal oxide diagnostic contrast agents and particularly metal oxides which exhibit superparamagnetic behaviour. In this case the oxide can function as a diagnostic contrast agent in EIT and magnetometric investigations and especially in MR imaging.

A wide range of metal oxides which exhibit superparamagnetic behaviour where the crystal size is beneath single domain size are well known and are described for example in U.S. Pat. No. 4,827,945 (Groman), EP-A-525199 (Meito Sangyo), and EP-A-580878 (BASF) . Mixed ferrites, containing more than one metal species, eg as referred to by BASF, may provide particularly effective crystals in terms of relaxivity. These various metal oxides may be used according to the present invention, but particularly preferred are iron oxide superparamagnetic crystals, eg compounds of formula $(FeO)_n Fe_2O_3$ when n is in the range 0 to 1, typified by maghemite ($\gamma$-$Fe_2O_3$) and magnetite ($Fe_3O_4$) as well as composites thereof. With the use of such iron oxide crystals, their uptake metabolism, generally by the reticuloendothelial system, releases no abnormal toxic metal, the iron simply being added to the body's iron reservoir.

Crystal size for superparamagnetic crystals will preferably be in the range 2 to 50 nm, especially 3 to 35 nm, and particularly 4 to 20 nm. The composite crystal/coating agent particles may contain single crystals or, if desired, multiple crystal clusters. In the latter case, the cluster "core" to the composite particle is desirably less than 100 nm in size.

Crystal, cluster and composite a particle sizes can easily be determined by standard techniques such as electron microscopy, laser light scattering or hydrodynamic chromatography, eg as discussed below before the Examples.

The weight ratio of metal oxide crystal to coating agent can readily be determined by elemental analysis such as by inductive coupled plasma analysis, eg comparing the signals for the metal of the metal oxide and the sulphur in the sulphate attachment groups of the coating agent (or analogously the signal of other characteristic atoms or groups of the coating agents where it is not a sulphate). Similarly, the ratio can be determined by gravimetric analysis.

The polvionic nature of the coating compounds enables them to bind to the crystal surface at a plurality of attachment sites per polymer molecule. This gives rise to a strong coating:crystal bonding which is capable of withstanding the conditions routinely used for autoclaving diagnostic agents (121° C. for 15 minutes) and gives a product which does not have the poor colloidal stability encountered, as mentioned above, with dextran: iron oxide products.

As a result of its polyionic nature, the coating agent gives the composite particles an overall electrical charge, detectable as a non-zero zeta potential. At especially low coating densities, the charge on the coating agent can balance out the charge of the metal oxide crystals and it is found that at the isoelectric point particle stability is poor and particle aggregation may occur giving aggregates over 1000 nm in size. This is undesirable, but the effect of coating level on particle size can readily be monitored and such aggregates avoided. In general zeta potentials having absolute values of at least 10 mV (ie $\leq -10$ mV or $\geq +10$ mV), especially 20 to 100 mV and particularly 30 to 70 mV are preferred.

Thus in a preferred embodiment the contrast agent of this invention comprises iron oxide core that is coated and stabilized by polyionic polysaccharides or polyaminoacids. The coated iron oxide particles show good stability when subjected to high temperatures, when diluted and over time. Compared to the conventional iron oxide preparations coated and stabilized by the storage polysaccharides dextran (or its derivatives) and starch, the new agents have a low toxicity and high biocompatibility To obtain an iron oxide preparation with a specific chemical composition and structure, carefully controlled preparation conditions are required. Many industrial applications of colloidal iron oxide suspensions (ferrofluids) have been described for recording technology, as dye and paint ingredients, and for electromechanical devices. Numerous methods for synthesis and stabilization of technical grade iron oxides exist, however, they are not applicable for pharmaceutical iron oxides, mainly because of their non-aqueous nature, and/or due to the toxicity of the applied coatings and surfactants.

The most commonly used method for synthesizing superparamagnetic iron oxide contrast agents derives from a procedure originally described by Molday (see Molday and Mackinzie, J. Immunol. Meth 52:353–367 (1982) and U.S. Pat. No. 4,452,773 (Molday)) for labelling and separation of biological molecules and cells. The so-called Molday-method, or one-step co-precipitation method, is based on the precipitation of iron oxides in an alkaline solution containing a water-soluble polysaccharide, preferably dextran. The colloidal sized composite particles comprise single or multiple iron oxide crystals embedded in, or coated with, dextran. The crystals are typically of magnetite or magnetite/maghemite structure with a size of 3–30 nm. The total particle diameter, however, may range from a low of about 10 nm to a high of several hundred nm. Typically, iron oxide preparations prepared by the Molday-method are inhomogeneous and multiple particle size fractions are detected in these preparations.

Centrifugation, filtration, or gel filtration methods have therefore been used in order to isolate particles within a more uniform size range (see Weissleder et al., Radiology 175:489–493 (1990)).

Conventional coated iron oxide particles with an overall diameter in the range of 50–1000 nm have been experimentally tested as liver and spleen contrast agents. Smaller, isolated particles have shown a prolonged blood half-life time and also the ability to cross the capillary wall. Potential applications for these agents are many, such as for imaging of the lymph nodes and bone marrow, for perfusion/blood pool imaging, and for active targeting. The dextran based agents however have been shown to be relatively unstable and to give significant adverse effects. As an example, an agent currently being used in clinical trials cannot be formulated as a ready-to-use product. The dose is diluted immediately before administration and injected as a slow infusion through an in-line filter in order to decrease the frequency and severity of adverse events such as blood pressure suppression, lower back pain and hematological changes.

We have found that the particles of the present invention have improved stability and toxicity as compared to the conventional particles. These particles used according to the invention may for example be synthesized by a simple two-step procedure where Step 1 is the precipitation of metal oxide crystals from an alkaline solution and Step 2 is a procedure of coating the crystals with a polymer of polyelectrolyte character, or alternatively, they may be synthesized by co-precipitation of metal oxide crystals and the polyelectrolyte coating polymer.

Metal oxide crystals can generally be precipitated from aqueous solutions of soluble salts of the metal(s) by addition of a base. Superparamagnetic iron oxide crystals may be precipitated from an aqueous solution of a mixture of iron salts by rapid addition of a base to pH above 10 while stirring vigorously or during sonication. A wide range of iron salts may be used such as $FeCl_2.nH_2O$, $FeCl_3.nH_2O$, Fe(III) citrate, Fe(II) gluconate, $FeSO_4.nH_2O$, $Fe_2(SO_4)_3$, Fe(II) oxalate, $Fe(NO_3)_3$, Fe(II) acetylacetonate, Fe(II) ethylenediammonium sulfate, Fe(II) fumarate, Fe(III) phosphate, Fe(III) pyrophosphate, ammonium Fe(III)citrate, ammonium Fe(II)sulfate, ammonium Fe(III) sulfate and ammonium Fe(II) oxalate. The ratio between ferrous and ferric iron should preferably be within the range of 1:5 to 5:1. Such precipitated iron oxide crystals can be represented by the following formula: $(FeO)_x.Fe_2O_3$ where x can be a number in the range of $\leq x \leq 1$. Maghemite, $\gamma\text{-}Fe_2O_3$, represents the lower x-value while magnetite, $Fe3O_4$, represents the upper value for x.

The bases used may be selected from a wide range of strong inorganic or organic bases such as NaOH, $Nh_4OH$, LiOH, KOH, triethylamine and guanidine. In general, the counterions for the metal and the base should be physiologically tolerable ions so as to minimise the need for the precipitated crystals to be cleansed of potentially toxic by-products.

The precipitation of iron oxide or, alternatively, the co-precipitation of iron oxide and the polymer, can take place in water, a mixture of water and organic solvent(s), or in a viscous medium. As an example, organic solvents like methanol, ethanol, acetone, ethers, and hexane may be used. The viscous matrix may consist of hydrogels of polysaccharides or polyamines, tri-iodinated aromatics, glycerol or polyethylene- and polypropylene-glycols. Precipitation from aqueous solution free from non-physiologically tolerable co-solvents is of course preferred as again the need for post-production purification is reduced.

The coating material as one of the components of the new iron oxide preparation has a polyelectrolyte structure because of advantages from the standpoint of stability and toxicity. The polyelectrolytes include polyanionic and polycationic compounds or a mixture of these that bind strongly to the iron oxide surface through multiple attachment points.

The coating materials can be grouped depending on their charge and functional groups, such as negatively charged polymers with functional groups containing phosphorus or sulphur atoms or carboxy groups, and positively charged polymers with functional groups containing nitrogen atoms. Examples of the negatively charged polymers are certain modifications of carboxycellulose, alginates, carrageenans, polygalacturonate, heparins and heparinoid compounds such as chrondroitin-4-sulphate, dermatansulphate, keratin sulphate and hyaluronate, synthetic polymers such as polystyrenesulphonate and aminoacids such as polyglutamate and polyaspartate. Examples of positively charged polymers include chitosan and polylysine.

As discussed above, the substitution degree and charge density of the polyelectrolyte polymers should not be too low where toxicity and stability of the particles become critical. The polymers must therefore contain multiple (more than one) functional groups to secure multiple attachment points to the metal oxide crystals and give the particles a charged surface.

The diameter of the superparamagnetic iron oxide core will generally be in the range of about 4 nm to about 100 nm. The smaller cores will contain only one subdomain superparamagnetic crystal while the larger cores may contain a cluster of crystals. The small diameter single crystal cores can be stabilized by low amounts of low or high molecular weight polymers, while larger quantities of polymers are needed to coat and stabilize the clusters due to their density and also the higher magnetic load per particle. The overall composite particle diameter, including the iron oxide core and the polymer coating layer, will generally lie in the range of from about 5 nm to 300 nm, depending upon the preparation conditions and the molecular weight, structure and amount of the polymer.

The relaxivity of the superparamagnetic iron oxide crystal containing particles will vary with the size and composition of the core and of the coated particle. The $T_1$ relaxivity ($r_1$) may be as low as 5 and as high as 200, while $T_2$ relaxivity ($r_2$) may vary between 5 and 500 at 0.5 T (relaxivity given as $s^{-1}mM^{-1}$ Fe). The $r_2/r_1$ ratio may vary from 1 to above 100, or preferably from 2 to 10. Small single crystal particles will have $r_2/r_1$ ratios in the lower range while larger particles and multicrystal particles will show higher ratios. The magnetization of the particles will be relatively independent of particle and crystal size as long as the iron oxide crystals show superparamagnetic behavior. At 1 T the magnetization is about 20–100, or preferably 30–90 emu/g iron oxide.

Viewed from a further aspect, the invention provides diagnostic compositions comprising the diagnostic agents of the invention together with at least one physiologically acceptable carrier or excipient, eg water for injections.

The compositions of the invention may be in any conventional pharmaceutical form, eg suspension, dispersion, powder etc. and may contain aqueous vehicles (such as water for injections) and/or ingredients to adjust osmolality, pH, viscosity, and stability. Ideally, the composition is in suspension form with the suspension being isotonic and isohydric with blood. For example, an isotonic suspension can be prepared by the addition of salts like sodium chloride, low-molecular weight sugars like glucose (dextrose), lactose, maltose, or mannitol or a soluble fraction of the polymer coating agent or a mixture of these. Isohydricity can be achieved by the addition of acids like hydrochloric acid or bases like sodium hydroxide if only a minor adjustment of pH is required. Buffers such as phosphate, citrate, acetate, borate, tartrate, and gluconate may also be used. The chemical stability of the particle suspension can be modified by the addition of antioxidants like ascorbic acid or sodium pyrosulphite and chelating agents like citric acid, sodium EDTA and sodium calcium EDTA. Excipients may also be added to improve the physical stability of the preparation. Most frequently used excipients for parenteral suspensions are surfactants like polysorbates, lecithin or sorbitan esters, viscosity modifiers like glycerol, propyleneglycol and polyethylene glycols (macrogols), or cloud point modifiers, preferably non-ionic surfactants.

The compositions of the invention will advantageously contain the metal oxide at a diagnostically effective metal concentration, generally 0.1 to 250 mg Fe/ml, preferably 1 to 100 mg Fe/ml, and especially preferably 5 to 75 mg Fe/ml.

The invention further provides a method of generating a contrast enhanced image of a human or non-human, preferably mammalian, body said method comprising administering to said body, preferably parenterally and especially preferably intravascularly, a suspension of a contrast agent according to the invention and generating an image of at least a part of said body into which said agent distributes, eg by MR, ET or magnetometry.

For the method of the invention, the dosage used will be a contrast effective dosage for the imaging modality used. Generally this will lie in the region 1 to 500 $\mu$mol Fe/kg, preferably 2 to 250 $\mu$mol Fe/kg and especially preferably 5 to 50 $\mu$mol Fe/kg.

Dosages and concentrations conventional in the art may be used.

Various iron oxide preparations prepared according to the prior art are known to give significant adverse effects when administered intravascularly. The most frequently reported findings are suppression of systemic blood pressure and acute platelet depletion. We have found that these side effects are physiological and hematological responses to particle induced activation of the complement system. While conventional iron oxide particles strongly activate the complement cascade, the composite particles of the present invention have no or only minor influence on the number of circulating platelets while conventional preparations cause an acute marked and transient thrombocytopenia. Foreign surfaces of carbohydrate nature, such as unmodified dextran and certain dextran modifications, can be potent activators of complement similar to many strains of gram-positive and gram-negative bacteria. The surfaces activate the alternative complement pathway because nucleophilic surface groups such as OH form a covalent bond with the C3b complement protein (see Immunology (second Edition), Gower Medical Publishing, New York, 1989; 13.3). Under circumstances of sepsis, the consequences of complement activation may be beneficial as the complement system is an important part of the body's reaction to an injury such as invasion by an infectious agent. However, following an injection of a particulate contrast agent, complement activation is deleterious rather than beneficial.

The coated particles of the present invention have surprisingly been shown to have no effect on the complement system or on complement related parameters such as the blood pressure and platelet count. The selected coating material gives rise to a particle surface that will not trigger complement activation in a similar manner to the conventional particles. Similarly, the low amount of polyelectrolyte polymers used to stabilize the particles also has a suppressive effect on complement activation, probably because of changes in opsonization (degree and type of opsonines) when compared to the conventional particles.

DETAILED DESCRIPTION OF THE INVENTION

The present invention will now be described in further detail in with reference to the following non-limiting Examples:

In the following Examples, the iron concentrations were determined by digestion of the iron oxide particles followed by analysis by ICP. pH was measured by using a Beckman φ10 pH meter equipped with an Orion Sureflow Ross pH electrode. The particle size distribution was measured by hydrodynamic chromatography (HDC) (see Small and Langhorst, Analytical Chem. 54:892A–898A(1982)) or by laser light scattering (PCS) using a Malvern Zetasizer 4. The particle surface charge, expressed as the zeta-potential or electrophoretic mobility, was also determined by a Malvern Zetasizer 4. The $T_1$ and $T_2$ relaxivity, $r_1$ and r2, were measured in aqueous samples at 37° C. and 0.47 T (Minispec PC-20). An IR pulse sequence was used for $T_1$ and a CPMG sequence (TE=4 ms) for $T_2$. Magnetization curves were obtained at ambient temperature on a vibrating sample magnetometer (Molspin) operating at magnetic fields from +1 to −1 T.

REFERENCE EXAMPLE 1

Dextran (5 g, Sigma) having a mean molecular weight of 9,000 D was dissolved in water (10 ml). At a temperature of 60° C., $FeCl_3.6H_2O$ (1.35 g) and $FeCl_2.4H_2O$ (0.81 g) were dissolved in the carbohydrate solution whereafter the mixture was slowly precipitated into 0.18M NaOH (100 ml) at 60° C. while sonicating. The sonication was continued for another 10 minutes followed by a centrifugation at 4000 rpm for 5 minutes. The supernatant was collected and a fraction dialyzed against 0.9% NaCl (5×1 L). The dextran particles exhibit a polydisperse particle size with a fraction being less than 12 nm and a fraction being larger than 300 nm measured by HDC.

REFERENCE EXAMPLE 2

(According to Example 7.3 of U.S. Pat. No. 5,314, 679)

To an aqueous solution (8.5 ml) of $FeCl_3.6H_2O$ (1.17 g) and $FeCl_2.4H_2O$ (0.53 g) was added 1M sodium carbonate to pH 2.3 and then dextran having a mean molecular weight of 9,000 D (5.00 g) was added. The solution was heated to 60–70° C. and then cooled to approximately 40° C. 7.5% $NH_4OH$ was added to pH approximately 9.5 before the suspension was heated to 95° C. for 15 minutes. The dispersion was dialysed against water (5×1L) (cutoff 15,000 dalton).

REFERENCE EXAMPLE 3

(According to Example 6.1 of U.S. Pat. No. 54, 770,183)

A solution of 50 ml of 0.28 M $FeCl_3$, 0.16M $FeCl_2$ and 6.25 g dextran having a mean molecular weight of 70,000 D (Pharmacia, Uppsala, Sweden) was added 50 ml 7.5% $NH_4OH$ over three minutes. The suspension was stirred for 5 minutes and then heated to 700° C. for 30 minutes. The solution was centrifugated at 5000 rpm for 15 minutes and the supernatant was dialyzed against water (5×1 L).

REFERENCE EXAMPLE 4

Starch (3 g, Reppe Glucose, Sweden) having a mean molecular weight of 70,000 D was dissolved in water (10 ml). At a temperature of 60° C., $FeCl_3.6H_2O$ (2.7 g) and $FeCl_2.4H_2O$ (4.5 g) was dissolved in the carbohydrate solution whereafter the mixture was slowly precipitated into 1.2 M NaOH (50 ml) at 60° C. while sonicating. The sonication was continued for another 10 minutes followed by a centrifugation at 5000 rpm for 5 minutes. The supernatant was collected and dialyzed against an aqueous solution of 0.9% NaCl. A magnetization curve revealed that the starch particles were superparamagnetic. The particle size was 450 nm measured by PCS. The size of the magnetite crystals were measured to be approximately 10 nm.

REFERENCE EXAMPLE 5 a) A dispersion of magnetite particles prepared as in Example 1a (equal to 0.3 g magnetite particles) was diluted with water (50 ml) and to this was added carboxy dextran with a mean molecular weight of 65,000 D (30 mg, Pharmacia Ab, Uppsala, Sweden) dissolved in water (30 ml). The dispersion was sonicated, centrifuged at 5000 rpm for 13 minutes and the supernatant filtered (0.22 μm filter). The carboxy dextran particles exhibited a mean diameter of 88 nm measured by HDC. The zeta-potential was measured to be −26 mV.

b) A dispersion of magnetite particles prepared as in Example 1a (equal to 0.3 g magnetite particles) was diluted with water (50 ml) and to this was added carboxy dextran with a mean molecular weight of 65,000 D(50 mg, Pharmacia Ab, Uppsala, Sweden) dissolved in water (5 ml). The dispersion was sonicated, centrifuged at 5000 rpm for 13 minutes and the supernatant filtered (0.22 μm filter). The carboxy dextran particles exhibited a mean diameter of 74 nm measured by HDC. The zeta-potential was measured to be −32 mV. The r1 was 35.2 $(mM.sec)^{-1}$ and r2 was 358 $(mM.sec)^{-1}$.

c) A dispersion of magnetite particles prepared as in Example 1a (equal to 0.3 g magnetite particles) is diluted with water (50 ml) and to this is added carboxy dextran with a molecular weight of 3,000–4,000 D(15 mg) dissolved in water (1.5 ml). The dispersion is sonicated, centrifuged at 5000 rpm for 13 minutes and the supernatant is filtered.

REFERENCE EXAMPLE 6 a) A dispersion of magnetite particles prepared as in Example 1a (equal to 0.5 g magnetite particles) was diluted with water (85 ml) and to this was added dextran phosphate with a mean molecular weight of 74,000 D(50 mg, Pharmacia Ab, Uppsala, Sweden) dissolved in water (5 ml). The dispersion was sonicated, centrifuged and the supernatant filtered (0.22 μm filter). A magnetization curve revealed that the dextran phosphate particles were superparamagnetic. The particle size was 74 nm measured by PCS.

b) A dispersion of magnetite particles prepared as in Example 1a (equal to 0.3 g magnetite particles) was diluted with water (50 ml) and to this was added dextran phosphate with a mean molecular weight of 71,800 D(50 mg, TdB Consultancy AS, Uppsala, Sweden) dissolved in water (5 ml). The dispersion was sonicated, centrifuged 5000 rpm for 13 minutes and the supernatant filtered (0.22 µm). The dextran phosphate particles exhibit a mean diameter of 48 nm measured by HDC. The zeta-potential was measured to be −51 mV. The r1 was 37 $(mM.sec)^{-1}$ and r2 was 342 $(mM.sec)^{-1}$.

c) A dispersion of magnetite particles prepared as in Example 1a (equal to 0.3 g magnetite particles) was diluted with water (50 ml) and to this was added dextran phosphate with a mean molecular weight of 71,800 D(15 mg, TdB Consultancy AB, Uppsala, Sweden) dissolved in water (1.5 ml). The dispersion was sonicated, centrifuged at 5000 rpm for 13 minutes and the supernatant filtered (0.22 µm filter). The dextran phosphate particles exhibit a mean diameter of 48 nm measured by HDC. The zeta potential was measured to be −36 mV.

REFERENCE EXAMPLE 7

A dispersion of magnetite particles from Example 1a (equal to 0.3 g magnetite particles) was diluted with water (50 ml) and to this was added dextran sulphate having a mean molecular weight of 500,000 D (30 mg, Sigma, D-6001) dissolved in water. The dispersion was sonicated, centrifuged at 5000 rpm for 13 minutes and the supernatant filtered (0.22 µm filter). A magnetization curve revealed that the dextran sulphate particles were superparamagnetic and they exhibit a mean diameter of 42 nm measured by HDC. The zeta-potential was measured to be −57 mV. Fifty six percent of the dextran sulphate was adsorbed on the particle surface. The r1 was 37.7 $(mM.sec)^{-1}$ and r2 relaxivity 307 $(mM.sec)^{-1}$.

Example 1 a) Magnetite particles were precipitated from an aqueous solution (500 ml) of $FeCl_2.4H_2O$ (12.50 g, 6.29×10⁻² mol) and $FeCl_3.6H_2O$ (33.99 g, 1.26×10⁻¹ mol) by quick addition of $NH_4OH$ (28–30%, 72 ml) to pH above 10 while stirring vigorously. The particles were collected magnetically and washed with water to pH 6–7. The particles were dispersed in approximately 200 ml of water. The reaction mixture was kept under nitrogen except for decanting and redispersing. Bare magnetite particles stabilized by HCl (pH 3.5) exhibited a mean hydrodynamic diameter of 97 nm. The zeta potential was measured to be +36 mV. The r1 was 27.8 $(mM.sec)^{-1}$ and the r2 324 $(mM.sec)^{-1}$.

b) A dispersion of magnetite particles from Example 1a (equal to 0.5 g magnetite particles) was diluted with water (70 ml) and to this was added heparin (2 ml, Heparin 5000 lU/ml, Prod.no. Fl NA, Nycomed Pharma, Oslo, Norway). The dispersion was sonicated, centrifuged at 4000 rpm for 13 minutes and the supernatant filtered (0.22 µm filter). A magnetization curve revealed that the heparin particles were superparamagnetic and they exhibited a mean diameter of 48 nm measured by HDC. The size of the magnetite crystals was measured to be approximately 10 nm by electron microscopy. The zeta potential was measured to be −61 mV. Fifty-four percent of the heparin was adsorbed to the particle surface corresponding to 10 µg sulphur per mg iron. The r1 was 40.5 $(mM.sec)^{-1}$ and r2 304 $(mM.sec)^{-1}$.

c) A dispersion of magnetite particles from Example 1a (equal to 0.5 g magnetite particles) was diluted with water (90 ml) and to this was added low molecular weight heparin, molecular weight of 4,000–6,000 D(0.8 ml Fragmin 10,000 lU/ml, Kabi Pharmacia AB, Sweden). The dispersion was sonicated, centrifuged at 4000 rpm for 13 minutes and the supernatant filtered (0.22 µm filter). A magnetization curve revealed that the heparin particles were superparamagnetic. Saturation magnetization was measured to be 78 emu/g iron oxide. The particle size was 85 nm measured by PCS. The zeta-potential was measured to be −40 mV. Sixteen percent of the polyelectrolyte added was adsorbed on the particle surfaces.

d) A dispersion of magnetite particles from Example 1a (equal to 0.5 g magnetite particles) was diluted with water (70 ml) and to that was added heparin (1 ml, Heparin 5000 IU/ml, Prod.no. F1NA, Nycomed Pharma, Oslo, Norway). The dispersion was sonicated, centrifuged at 4000 rpm for 13 minutes and the supernatant filteed (0.22 µm filter). A magnetization curve revealed that the heparin particles were superparamagnetic and they exhibited a mean diameter of 64 nm measured by PCS. Sixty-nine percent of the heparin was adsorbed to the particle surface corresponding to 7 µg sulphur per mg iron. The r1 was 38 $(mM.sec)^{-1}$ and r2 273 $(mM.sec)^{-1}$.

Example 2

A dispersion of magnetite particles from Example 1a (equal to 0.3 g magnetite particles) was diluted with water (50 ml) and to this was added dermatan sulphate (36 mg, Sigma C-241 3) dissolved in water (5 ml). The dispersion was sonicated, centrifuged at 5000 rpm for 13 minutes and the supernatant filtered (0.22 µm filter). The dermatan sulphate particles exhibited a mean diameter of 49 nm measured by HDC. Forty percent of the dermatan sulphate was adsorbed on the particle surface. The zeta-potential was measured to be −58 mV.

Example 3

A dispersion of magnetite particles from Example 1a (equal to 0.3 g magnetite particles) was diluted with water (50 ml) and to this was added hyaluronic acid (60 mg, Sigma H-401 5) dissolved in water (6 ml). The dispersion was sonicated, centrifuged at 5000 rpm for 13 minutes and the supernatant filtered (0.22 µm filter). A magnetization curve revealed that the hyaluronic particles were superparamagnetic and they exhibit a mean diameter of 123 nm measured by HDC. The zeta-potential was measured to be −55 mV. The r1 was 33.7 $(mM.sec)^{-1}$ and r2 318 $(mM.sec)^{-1}$.

Example 4

A dispersion of magnetite particles from Example 1a (equal to 0.3 g magnetite particles) was diluted with water (50 ml) and to this was added chondroitin-4-sulphate (60 mg, Sigma C-8529) dissolved in water (5 ml). The dispersion was sonicated, centrifuged at 5000 rpm for 13 minutes and the supernatant filtered (0.22 µm filter). A magnetization curve revealed that the chondroitin-4-sulphate particles were superparamagnetic and they exhibit a mean diameter of 54 nm measured by HDC. The zeta-potential was measured to be −52 mV. Twenty-nine percent of the chondroitin-4-sulphate was adsorbed on the particle surface. The r1 was 40.4 $(mM.sec)^{-1}$ and r2 314 $(mM.sec)^{-1}$.

Example 5

The iron oxide formulations from Reference Example 7 (dextran sulphate iron oxide) and Examples 1b and d (heparin iron oxide) were incubated with human plasma in vitro in a concentration equivalent to a dosage of 1 mg Fe/kg and their effect on the coagulation parameter activated partial thromboplastin time (APTT) was studied by use of Cephotest™ (Nycomed Pharma AS). The heparin iron oxide formulations in Examples 1b and d prolonged the APTT in a heparin dose-dependent manner by factors of 4.5 and 2.5, respectively. This clearly shows the desirability of minimising the coating density used. The formulation in Reference Example 7 prolonged APTT by a factor of 2.7.

Example 6

The iron oxide formulations from Examples 1b and d (heparin iron oxide) were administered intravenously to rats (n=3) at dosages of 1 mgFe/kg (1b only) and 2 mgFe/kg and blood samples were withdrawn before and 10, 30 and 60 minutes after injection. The effect of the formulations on the coagulation parameter activated partial thromoboplastin time (APTT) was studied in vitro by use of Chepotest™ (Nycomed Pharma AS). The formulations prolonged the APTT in a dose- and time-dependent manner. At 10 and 30 minutes after injection, the 2 mgFe/kg dosage of the formulations of Examples 1b and d prolonged APTT by factors of 4 and 1.5, respectively. The 1 mgFe/kg dosage of the Example 1b formulation prolonged APTT by a factor of 1.3 at 10 minutes.

Example 7

A dispersion of magnetite particles from Example 1a (equal to 0.1 g magnetite particles) is diluted with water (15 ml) and to this is added heparan sulphate(20 mg, Sigma H-7641) dissolved in water. The dispersion is sonicated and centrifuged. The supernatant is collected.

Example 8

A dispersion of magnetite particles from Example 1a (equal to 0.1 g magnetite particles) is diluted with water (15 ml) and to this is added keratan sulphate (15 mg, Sigma K-3001) dissolved in water. The dispersion is sonicated and centrifuged. The supernatant is collected.

Example 9 a) A dispersion of magnetite particles from Example 1a (equal to 0.3 g magnetite particles) is diluted with water (50 ml) and to this is added lambda-carrageenan (30 mg, Sigma C-3889) dissolved in water (3 ml). The dispersion was sonicated, centrifuged at 4000 rpm for 13 minutes and filtered (0.22 μm filter). The lambda-carrageenan particles exhibit a mean diameter of 53 nm measured by HDC. The zeta-potential was measured to be −56 mV.

b) A dispersion of magnetite particles from Example 1a (equal to 0.3 g magnetite particles) is diluted with water (50 ml) and to this is added lambda-carrageenan (50 mg, Sigma C-3889) dissolved in water (5 ml). The dispersion was sonicated, centrifuged at 4000 rpm for 13 minutes and filtered (0.22 μm filter). The lambda-carrageenan particles exhibited a mean diameter of 61 nm measured by HDC. The zeta-potential was measured to be −61 mV. The r1 was 38.6 $(mM.sec)^{-1}$ and r2 309 $(mM.sec)^{-1}$.

c) A dispersion of magnetite particles from Example 1a (equal to 0.3 g magnetite particles) is diluted with water (50 ml) and to this is added lambda-carrageenan (15 mg, Sigma C-3889) dissolved in water (1.5 ml). The dispersion was sonicated, centrifuged at 4000 rpm for 13 minutes and filtered (0.22 μm filter). The lambda-carrageenan particles exhibited a mean diameter of 52 nm measured by HDC. The zeta-potential was measured to be −50 mV.

Example 10 a) A dispersion of magnetite particles from Example 1a (equal to 0.3 g magnetite particles) is diluted with water (50 ml) and to this is added iota-carrageenan (30 mg, Fluka Prod 22045) dissolved in water (3 ml). The dispersion was sonicated, centrifuged at 5000 rpm for 13 minutes and filtered (0.22 μm filter). The iota-carrageenan particles exhibited a mean diameter of 63 nm measured by HDC. The zeta-potential was measured to be −47 mV.

b) A dispersion of magnetite particles from Example 1a (equal to 0.3 g magnetite particles) is diluted with water (50 ml) and to this is added iota-carrageenan (15 mg, Fluka 22045) dissolved in water (1.5 ml). The dispersion was sonicated, centrifuged at 5000 rpm for 13 minutes and filtered (0.22 μm filter). The iota-carrageenan particles exhibited a mean diameter of 54 nm measured by HDC. The zeta-potential was measured to be −39 mV.

Example 11 a) A dispersion of magnetite particles from Example 1a (equal to 0.5 g magnetite particles) was diluted with water (80 ml) and to this was added alginate Protanal LP 10/60 having a mean molecular weight of approx. 180,000 D(50 mg, Pronova, Drammen, Norway). dissolved in water (10 ml). The dispersion was sonicated, centrifuged at 5000 rpm for 13 minutes and the supernatant filtered (0.22 μm filter). The alginate particles exhibited a mean diameter of 57 nm measured by HDC. The zeta-potential was measured to be −63 mV. The r1 was 39.9 $(mM.sec)^{-1}$ and r2 305 $(mM.sec)^{-1}$.

b) A dispersion of magnetite particles from Example 1a (equal to 0.5 g magnetite particles) was diluted with water (80 ml) and to this was added alginate Protanal LF 60 having a mean molecular weight of approx. 325,000 D(25 mg, Pronova, Drammen, Norway) dissolved in water (10 ml). The dispersion was sonicated, centrifuged at 5000 rpm for 13 minutes and the supernatant filtered (0.22 μm filter). The alginate particles exhibited a mean diameter of 67 nm measured by HOC. The zeta-potential was measured to be −58 mV.

c) A dispersion of magnetite particles from Example 1a (equal to 0.3 g magnetite particles) was diluted with water (50 ml) and to this was added alginate Protanal LFR 5/60 having a mean molecular weight of approx. 380,000 D(15 mg, Pronova, Drammen, Norway) dissolved in water (15 ml). The dispersion was sonicated, centrifuged at 5000 rpm for 13 minutes and the supernatant filtered (0.22 μm filter). The alginate particles exhibit a mean diameter of 62 nm measured by HDC. The zeta-potential was measured to be −53 mV.

Example 12 a) A dispersion of magnetite particles from Example 1a (equal to 0.3 g magnetite particles) was diluted with water (50 ml) and to this was added sodium carboxy cellulose (30 mg) dissolved in water (3 ml). The dispersion was sonicated, centrifuged at 5000 rpm for 13 minutes and the supernatant filtered (0.22 μm filter). The carboxy cellulose particles exhibited a mean diameter of 56 nm measured by HDC. The zeta-potential was measured to be −57 mV. The r1 was 40.1 $(mM.sec)^{-1}$ and r2 303 $(mM.sec)^{-1}$.

b) A dispersion of magnetite particles from Example 1a (equal to 0.3 g magnetite particles) was diluted with water (50 ml) and to this was added sodium carboxy cellulose (15 mg) dissolved in water (1.5 ml). The dispersion was sonicated, centrifuged at 5000 rpm for 13 minutes and the supernatant filtered (0.22 μm filter). The carboxy cellulose particles exhibited a mean diameter of 65 nm measured by HDC. The zeta-potential was measured to be −53 mV.

Example 13 a) A dispersion of magnetite particles from Example 1a (equal to 0.3 g magnetite particles) was diluted with water (50 ml) and to this was added chitosan having a molecular weight of approx. 2000,000 D(30 mg, Fluka 22743) dissolved in 1% acetic acid (4.5 ml). The dispersion was sonicated, centrifuged at 5000 rpm for 13 minutes and the supernatant filtered (0.22 µm filter). A magnetization curve revealed that the chitosan particles were superparamagnetic. The particle size was 64 nm measured by PCS. The zeta-potential was measured to be +48 mV. The r1 was 35.1 $(mM.sec)^{-1}$ and r2 281 $(mM.sec)^{-1}$.

b) A dispersion of magnetite particles from Example 1a (equal to 0.3 g magnetite particles) was diluted with water (50 ml) and to this was added chitosan having a molecular weight of approx. 2000,000 D(50 mg, Fluka 22743) dissolved in 1% acetic acid (7.5 ml). The dispersion was sonicated, centrifuged at 5000 rpm for 13 minutes and the supernatant filtered (0.22 µm filter). A magnetization curve revealed that the chitosan particles were superparamagnetic. The particle size was 64 nm measured by PCS. The zeta-potential was measured to be +47 mV.

c) A dispersion of magnetite particles from Example 1a (equal to 0.3 g magnetite particles) was diluted with water (50 ml) and to this was added chitosan having a molecular weight of approx. 2000,000 D(15 mg, Fluka 22743) dissolved in it acetic acid (2.25 ml). The dispersion was sonicated, centrifuged at 5000 rpm for 13 minutes and the supernatant filtered (0.22 µm filter). A magnetization curve revealed that the chitosan particles were superparamagnetic. The particle size was 64 nm measured by PCS. The zeta-potential was measured to be +47 mV.

Example 14 a) A dispersion of magnetite particles from Example 1a (equal to 0.3 g magnetite particles) was diluted with water (50 ml) and to this was added chitosan having a molecular weight of approx. 750,000 D(50 mg, Fluka 22742) dissolved in 1% acetic acid (7.5 ml). The dispersion was sonicated, centrifuged at 5000 rpm for 13 minutes and the supernatant filtered (0.22 µm filter). A magnetization curve revealed that the chitosan particles were superparamagnetic. The particle size was 62 nm measured by PCS. The zeta-potential was measured to be +48 mV. The r1 was 33.4 $(mM.sec)^{-1}$ and r2 279 $(mM.sec)^{-1}$.

b) A dispersion of magnetite particles from Example 1a (equal to 0.3 g magnetite particles) was diluted with water (50 ml) and to this was added chitosan having a molecular weight of approx. 750,000 D(15 mg, Fluka 22742) dissolved in 1% acetic acid (2.25 ml). The dispersion was sonicated, centrifuged at 5000 rpm for 13 minutes and the supernatant filtered (0.22 µm filter). A magnetization curve revealed that the chitosan particles were superparamagnetic. The particle size was 64 nm measured by PCS. The zeta-potential was measured to be +49 mV.

Example 15 a) A dispersion of magnetite particles from Example 1a (equal to 0.3 g magnetite particles) was diluted with water (50 ml) and to this was added chitosan having a molecular weight of approx. 70,000 D(30 mg, Fluka 22741) dissolved in 1% acetic acid (4.5 ml) . The dispersion was sonicated, centrifuged at 5000 rpm for 13 minutes and the supernatant filtered (0.22 µm filter). A magnetization curve revealed that the chitosan particles were superparamagnetic. The particle size was 62 nm measured by PCS. The zeta-potential was measured to be +49 mV. The r1 was 34.3 $(mM.sec)^{-1}$ and r2 327 $(mM.sec)^{-1}$.

b) A dispersion of magnetite particles from Example 1a (equal to 0.3 g magnetite particles) was diluted with water (50 ml) and to this was added chitosan having a molecular weight of approx. 70,000 D(15 mg, Fluka 22741), dissolved in 1% acetic acid (2.25 ml) . The dispersion was sonicated, centrifuged at 5000 rpm for 13 minutes and the supernatant filtered (0.22 µm filter) . A magnetization curve revealed that the chitosan particles were superparamagnetic. The particle size was 64 nm measured by PCS. The zeta-potential was measured to be +48 mV.

Example 16 a) A dispersion of magnetite particles from Example 1a (equal to 0.3 g magnetite particles) was diluted with water (50 ml) and to this was added poly(sodium 4-styrenesulfonate) (30 mg, Janssen 22.227.14) dissolved in water (3 ml). The dispersion was sonicated, centrifuged at 5000 rpm for 13 minutes and the supernatant filtered (0.22 µm filter). The poly(4-styrenesulfonate) particles exhibited a mean diameter of 43 nm measured by HDC. The zeta-potential was measured to be −53 mV.

b) A dispersion of magnetite particles from Example 1a (equal to 0.3 g magnetite particles) was diluted with water (50 ml) and to this was added poly(sodium 4-styrenesulfonate) (15 mg, Janssen 22.227.14) dissolved in water (1.5 ml). The dispersion was sonicated, centrifuged at 5000 rpm for 13 minutes and the supernatant filtered (0.22 µm filter). The poly(4-styrenesulfonate) particles exhibited a mean diameter of 36 nm measured by HDC. The zeta-potential was measured to be −49 mV.

Example 17 a) A dispersion of magnetite particles from Example 1a (equal to 0.3 g magnetite particles) was diluted with water (50 ml) and to this was added poly-L glutamic acid having a molecular weight of 2,000–15,000 D (30 mg, Sigma P-4636) dissolved in water (3 ml). The dispersion was sonicated, centrifuged at 4000 rpm for 13 minutes and the supernatant filtered (0.22 µm filter). A magnetization curve revealed that the poly-L-glutamic acid particles were superparamagnetic and they exhibited a mean diameter of 37 nm measured by HDC. The zeta-potential was measured to be −68 mV.

b) A dispersion of magnetite particles from Example 1a (equal to 0.3 g magnetite particles) was diluted with water (50 ml) and to this was added poly-L-glutamic acid having a molecular weight of 2,000–15,000 D (50 mg, Sigma P-4636) dissolved in water (5 ml). The dispersion was sonicated, centrifuged at 4000 rpm for 13 minutes and the supernatant filtered (0.22 µm filter). The poly-L-glutamic acid particles exhibited a mean diameter of 38 nm measured by HDC. The zeta-potential was measured to be −66 mV. The r1 was 40.4 $(mM.sec)^{-1}$ and r2 281 $(mM.sec)^{-1}$.

c) A dispersion of magnetite particles from Example 1a (equal to 0.3 g magnetite particles) was diluted with water (50 ml) and to this was added poly-L-glutamic acid having a molecular weight of 2,000–15,000 D (15 mg, Sigma P-4636) dissolved in water (1.5 ml). The dispersion was sonicated, centrifuged at 4000 rpm for 13 minutes and the supernatant filtered (0.22 µm filter). The poly-L-glutamic acid particles exhibited a mean diameter of 38 nm measured by HDC. The zeta-potential was measured to be −65 mV.

Example 18 a) A dispersion of magnetite particles from Example 1a (equal to 0.3 g magnetite particles) was diluted with water (50 ml) and to this was added poly-L-glutamic acid having a molecular weight of 15,000–50,000 D (30 mg, Sigma P-4761) dissolved in water (3 ml). The dispersion was sonicated, centrifuged at 4000 rpm for 13 minutes and the supernatant filtered (0.22 μm filter). The poly-L-glutamic acid particles exhibited a mean diameter of 37 nm measured by HDC. The zeta-potential was measured to be −66 mV.

b) A dispersion of magnetite particles from Example 1a (equal to 0.3 g magnetite particles) was diluted with water (50 ml) and to this was added poly-L-glutamic acid having a molecular weight of 15,000–50,000 D(50 mg, Sigma P4761) dissolved in water (5 ml). The dispersion was sonicated, centrifuged at 4000 rpm for 13 minutes and the supernatant filtered (0.22 μm filter). The poly-L-glutamic acid particles exhibited a mean diameter of 36 nm measured by HDC. The zeta-potential was measured to be −66 mV. The r1 was 41.7 $(mM.sec)^{-1}$ and r2 286 $(mM.sec)^{-1}$.

c) A dispersion of magnetite particles from Example 1a (equal to 0.3 g magnetite particles) was diluted with water (50 ml) and to this was added poly-L-glutamic acid having a molecular weight of 15,000–50,000 D (15 mg, Sigma P4761) dissolved in water (1.5 ml). The dispersion was sonicated, centrifuged at 4000 rpm for 13 minutes and the supernatant filtered (0.22 μm filter). The poly-L-glutamic acid particles exhibited a mean diameter of 36 nm measured by HDC. The zeta-potential was measured to be −63 mV.

a) A dispersion of magnetite particles from Example 1a (equal to 0.3 g magnetite particles) was diluted with water (50 ml) and to this was added poly-L-glutamic acid having a molecular weight of 50,000–100,000 D (30 mg, Sigma P-4886) dissolved in water (3 ml). The dispersion was sonicated, centrifuged a 4000 rpm for 13 minutes and the supernatant filtered (0.22 μm filter). A magnetization curve revealed that the poly-L-glutamic particles were superparamagnetic. The mean diameter was 40 nm measured by HDC. The zeta-potential was measured to be −70 mV. The r1 was 39.6 $(mM.sec)^{-1}$ and r2 289 $(nM.sec)^{-1}$.

b) A dispersion of magnetite particles from Example 1a (equal to 0.3 g magnetite particles) was diluted with water (50 ml) and to this was added poly-L-glutamic acid having a molecular weight of 50,000–100,000 D (15 mg, Sigma P-4886) dissolved in water (1.5 ml). The dispersion was sonicated, centrifuged at 4000 rpm for 13 minutes and supernatant filtered (0.22 μm filter). The mean diameter was 39 nm measured by HDC. The zeta-potential was measured to be −66 mV.

Example 20 a) A dispersion of magnetite particles from Example 1a (equal to 0.3 g magnetite particles) was diluted with water (50 ml) and to this was added poly-L-aspartic acid having molecular weight of 15,000–50,000 D (30 mg, Sigma P-6762) dissolved in water (3 ml). The dispersion was sonicated, centrifuged at 4000 rpm for 13 minutes and the supernatant filtered (0.22 μm filter). The mean diameter was 42 nm measured by HDC. The zeta-potential was measured to be −65 mV.

b) A dispersion of magnetite particles from Example 1a (equal to 0.3 g magnetite particles) was diluted with water (50 ml) and to this was added poly-L-aspartic acid having molecular weight of 15,000–50,000 D (50 mg, Sigma P6762) dissolved in water (5 ml). The dispersion was sonicated, centrifuged at 4000 rpm for 13 minutes and the supernatant filtered (0.22 μm filter). The poly-L-aspartic particles exhibited a mean diameter of 40 nm measured by HDC. The zeta-potential was measured to be −67 mV. The r1 was 40.8 $(mM.sec)^{-1}$ and r2 332 $(mM.sec)^{-1}$.

c) A dispersion of magnetite particles from Example 1a (equal to 0.3 g magnetite particles) was diluted with water (50 ml) and to this was added poly-L-aspartic acid having molecular weight of 15,000–50,000 D (15 mg, Sigma P-6762) dissolved in water (1.5 ml). The dispersion was sonicated, centrifuged at 4000 rpm for 13 minutes and the supernatant filtered (0.22 μm filter). The poly-L-aspartic particles exhibited a mean diameter of 44 nm measured by HDC. The zeta-potential was measured to be −66 mV.

Example 21 a) A dispersion of magnetite particles from Example 1a (equal to 0.3 g magnetite particles) was diluted with water (50 ml) and to this was added poly-L-aspartic acid having molecular weight of 5,000–15,000 D (30 mg, Sigma P 5387) dissolved in water (3 ml). The dispersion was sonicated, centrifuged at 4000 rpm for 13 minutes and the supernatant filtered (0.22 μm filter). The poly-L-aspartic particles exhibited a mean diameter of 38 nm measured by HDC. The zeta-potential was measured to be −67 mV. The r1 was 41.1 $(nM.sec)^{-1}$ and r2 303 $(sec)^{-1}$.

b) A dispersion of magnetite particles from Example 1a (equal to 0.3 g magnetite particles) was diluted with water (50 ml) and to this was added poly-L-aspartic acid having molecular weight of 5,000–15,000 D (50 mg, Sigma P5387) dissolved in water (5 ml). The dispersion was sonicated, centrifuged at 4000 rpm for 13 minutes and the supernatant filtered (0.22 μm filter). The poly-L-aspartic particles exhibited a mean diameter of 37 nm measured by HDC. The zeta-potential was measured to be −70 mV.

c) A dispersion of magnetite particles from Example 1a (equal to 0.3 g magnetite particles) was diluted with water (50 ml) and added poly-L-aspartic acid having molecular weight of 5,000–15,000 D (15 mg, Sigma P5387) dissolved in water (1.5 ml). The dispersion was sonicated, centrifuged at 4000 rpm for 13 minutes and the supernatant filtered (0.22 μA filter). The poly-L-aspartic particles exhibited a mean diameter of 37 nm measured by HDC. The zeta-potential was measured to be −65 mv.

Example 22 a) A dispersion of magnetite particles from Example 1a (equal to 0.3 g magnetite particles) was diluted with water (50 ml) and to this was added polyacrylic acid having a molecular weight of 2,000 D (30 mg, Aldrich 32,366-7) dissolved in water (3 ml). The dispersion was sonicated, centrifuged at 5000 rpm for 13 minutes and the supernatant filtered (0.22 μm filter)—The poly acrylic particles exhibited a mean diameter of 50 nm measured by HDC. The zeta-potential was measured to be −36 mV. The r1 was 29.1 $(mM.sec)^{-1}$ and r2 323 $(mM.sec)^{-1}$.

b) A dispersion of magnetite particles from Example 1a (equal to 0.3 g magnetite particles) was diluted with water (50 ml) and to this was added polyacrylic acid having a molecular weight of 2,000 D (50 mg, Aldrich 32,366-7) dissolved in water (5 ml). The dispersion was sonicated, centrifuged at 5000 rpm for 13 minutes and the supernatant filtered (0.22 μm filter). The polyacrylic particles exhibited a mean diameter of 57 nm measured by HDC. The zeta-potential was measured to be −29 mV.

c) A dispersion of magnetite particles from Example 1a (equal to 0.3 g magnetite particles) is diluted with water (50 ml) and to this was added polyacrylic acid having a molecular weight of 90,000 D (30 mg, Aldrich 19,205-8) dissolved in water (3 ml). The dispersion is sonicated, centrifuged and the supernatant filtered.

Example 23 a) A dispersion of magnetite particles from Example 1a (equal to 0.3 g magnetite particles) was diluted with water (50 ml) and to this was added polygalacturonic acid having a molecular weight of 25,000–50,000 D (30 m, Fluka 81325) dissolved in water (3 ml) with added thereto a few drops of 1 M NaOH. The dispersion was sonicated, centrifuged at 5000 rpm for 13 minutes and the supernatant filtered (0.45 μm filter). The polygalacturonic acid particles exhibited a mean diameter of 55 nm measured by HDC. The zeta-potential was measured to be −60 mV.

b) A dispersion of magnetite particles from Example 1a (equal to 0.3 g magnetite particles) was diluted with water (50 ml) and to this was added polygalacturonic acid having a molecular weight of 25,000–50,000 D (15 mg, Fluka 81325) dissolved in water (1.5 ml) with added thereto a few drops of 1 M NaOH. The dispersion was sonicated, centrifuged at 5000 rpm for 13 minutes and the supernatant filtered (0.45 μm filter). The polygalacturonic acid particles exhibited a mean diameter of 61 nm measured by HDC. The zeta-potential was measured to be −55 mV.

Example 24 a) A dispersion of magnetite particles from Example 1a (equal to 0.3 g magnetite particles) was diluted with water (50 ml) and to this was added poly-L-lysine having a molecular weight of 1,000–4,000 D (30 mg, Sigma P-0879) dissolved in water (3 ml). The dispersion was sonicated, centrifuged at 4000 rpm for 13 minutes and the supernatant filtered (0.45 μm filter). The particle size was 102 nm measured by PCS. The zeta potential was measured to be +47 mV.

b) A dispersion of magnetite particles from Example 1a (equal to 0.3 g magnetite particles) was diluted with water (50 ml) and to this was added poly-L-lysine having a molecular weight of 1,000–4,000 D (15 mg, Sigma P-0879) dissolved in water (1.5 ml). The dispersion was sonicated, centrifuged at 4000 rpm for 13 minutes and the supernatant filtered (0.45 μm filter). The particle size was 108 nm measured by PCS. The zeta potential was measured to be +46 mV.

Example 25 a) A dispersion of magnetite particles from Example 1a (equal to 0.3 g magnetite particles) was diluted with water (50 ml) and to this was added poly-L-lysine having a molecular weight of 15,000–30,000 (50 mg, Sigma P-7890) dissolved in water (5 ml). The dispersion was sonicated, centrifuged at 4000 rpm for 13 minutes and the supernatant filtered (0.22 μm filter). A magnetization curve revealed that the poly-L-lysine particles were superparamagnetic. The particle size was 78 nm measured by PCS. The zeta-potential was measured to be +56 mV. The r1 was 38.3 $(mM.sec)^{-1}$ and r2 295 $(mM.sec)^{-1}$.

b) A dispersion of magnetite particles from Example 1a (equal to 0.3 g magnetite particles) was diluted with water (50 ml) and to this was added poly-L-lysine having a molecular weight of 15,000–30,000 (15 mg, Sigma P-7890) dissolved in water (1.5 ml). The dispersion was sonicated, centrifuged at 4000 rpm for 13 minutes and the supernatant filtered (0.22 μm filter). The particle size was 89 nm measured by PCS. The zeta potential was measured to be +57 mV.

Example 26 a) A dispersion of magnetite particles from Example 1a (equal to 0.3 g magnetite particles) was diluted with water (50 ml) and to this was added poly-L-lysine having a molecular weight of 70,000–150,000 D (30 mg, Sigma P 1274) dissolved in water (3 ml). The dispersion was sonicated, centrifuged at 4000 rpm for 13 minutes and the supernatant filtered (0.22 μm filter). The particle size was 94 nm measured by PCS. The zeta potential was measured to be +57 mV.

b) A dispersion of magnetite particles from Example 1a (equal to 0.3 g magnetite particles) was diluted with water (50 ml) and to this was added poly-L-lysine having a molecular weight of 70,000–150,000 D (50 mg, Sigma P-1274) dissolved in water (5 ml). The dispersion was sonicated, centrifuged at 4000 rpm for 13 minutes and the supernatant filtered (0.22 μm filter). The particle size was 86 nm measured by PCS. The zeta potential was measured to be +62 mV. The r1 was 36.9 $(mM.sec)^{-1}$ and r2 294 $(mM.sec)^{-1}$.

c) A dispersion of magnetite particles from Example 1a (equal to 0.3 g magnetite particles) was diluted with water (50 ml) and to this was added poly-L-lysine having a molecular weight of 70,000–150,000 D (15 mg, Sigma P 1274) dissolved in water (1.5 ml). The dispersion was sonicated, centrifuged at 4000 rpm for 13 minutes and the supernatant filtered (0.22 μm filter). The particle size was 96 nm measured by PCS. The zeta potential was measured to be +61 mV.

Example 27 a) A dispersion of magnetite particles from Example 1a (equal to 0.3 g magnetite particles) was diluted with water (50 ml) and to this was added poly(Asp-Na, Glu-Na) 1:1 having a molecular weight of 5,000–15,000 D (30 mg, Sigma P 1408) dissolved in water (3 ml). The dispersion was sonicated, centrifuged at 5000 rpm for 13 minutes and the supernatant filtered (0.22 μm filter). A magnetization curve revealed that the poly(Asp.Na, Glu.Na) particles were superparamagnetic and they exhibited a mean diameter of 38 nm measured by HDC. The zeta-potential was measured to be −58 mV. The r1 was 40.4 $(mM.sec)^{-1}$ and r2 277 $(mM.sec)^{-1}$.

b) A dispersion of magnetite particles from Example 1a (equal to 0.3 g magnetite particles) was diluted with water (50 ml) and to this was added poly(Asp-Na, Glu-Na) 1:1 having a molecular weight of 5,000–15,000 D (15 mg, Sigma P1408) dissolved in water (1.5 ml). The dispersion was sonicated, centrifuged at 5000 rpm for 13 minutes and the supernatant filtered (0.22 μm filter). The poly(Asp.Na, Glu.Na) particles exhibited a mean diameter of 40 nm measured by HDC. The zeta potential was measured to be −60 mV.

Example 28

A dispersion of magnetite particles from Example 1a (equal to 0.3 g magnetite particles) was diluted with water (50 ml) and to this was added poly(Glu, GluOEt) 4:1 having a molecular weight of 70,000–150,000 D (30 mg, Sigma P4910) dissolved in ethanol (3 ml) with added thereto a few drops of HCl. The dispersion was sonicated, centrifuged and the supernatant collected.

Example 29 a) A dispersion of magnetite particles from Example 1a (equal to 0.3 g magnetite particles) was diluted with water (50 ml) and to this was added poly(Glu, Lys) 1:4 having a molecular weight of 150,000–300,000 D (30 mg, Sigma P0650) dissolved in water (5.7 ml). The dispersion was sonicated, centrifuged at 5000 rpm for 13 minutes and the supernatant filtered (0.22 µm filter). The poly(Glu, Lys) particles exhibited a mean diameter of 79 rm measured by HDC. The zeta-potential was measured to be +65 mV.

b) A dispersion of magnetite particles from Example 1a (equal to 0.3 g magnetite particles) was diluted with water (50 ml) and to this was added poly(Glu, Lys)1:4 having a molecular weight of 150,000–300,000 D (50 mg, Sigma P0650) dissolved in water (9.5 ml). The dispersion was sonicated, centrifuged at 5000 rpm for 13 minutes and the supernatant filtered (0.22 µm filter). The poly(Glu, Lys) particles exhibited a mean diameter of 77 nm measured by HOC. The zeta-potential was measured to be +63 mV. The r1 was 35.5 $(mM.sec)^{-1}$ and r2 255 $(mM.sec)^{-1}$.

Example 30

A dispersion of magnetite particles prepared as in Example 1a (equal to 0.3 g magnetite particles) is diluted with water (50 ml) and to this is added a dendrimer (prepared in accordance with U.S. Pat. No. 4,507,466 (The Dow Chemical Corporation)) (30 mg) in water. The dispersion is sonicated, centrifuged at 5000 rpm for 13 minutes and the supernatant collected.

Stability

Example 31

The stability of the following iron oxide formulations was tested by autoclaving at 121° C. for 15 minutes: Reference Examples 5b and 6b, Examples 1a, 1b, 2, 3, 4, 9a, 10a, 11a, b and c, 12a, 13a, b and c, 14b, 15a, 16a, 17a and b, 18b, 19a, 20a, 21b, 22a, 23a, 25a, 26a, 27b and 29a.

The uncoated iron oxide particles from Example 1a were dispersed by use of HCl before the experiment. No modifications were made for the other formulations. The formulations were inspected immediately before and after autoclaving as well as one day and one week later. The sample from Example 1a showed complete separation after autoclaving. The other formulations were not affected by the extreme heating and showed homogeneous size distribution before and at all points of time after autoclaving.

Example 32

Figure 1:
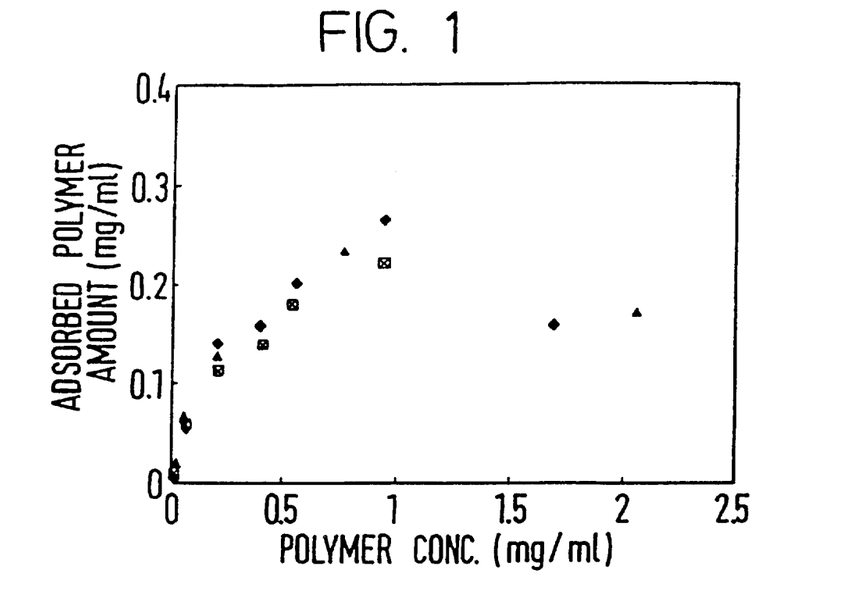
FIG. 1 is a graph which shows the amount of absorbed polymer on colloidal iron oxide versus the concentration of the polymer.

The adsorption of one typical example of the polyelectrolyte polymers of this invention, poly(sodium 4-styrene sulphonate) (PSSNa), was studied. Measurements of the adsorption isotherm as well as the electrophoretic mobility and particle size as function of polymer contraction were performed. The uncoated iron oxide particles from Example 1a were coated with PSSNa as described in Example 16, however, the dispersions were not sonicated. PSSNa amounts giving polymer to iron oxide ratios of $9 \times 10^{-3}$ to 2.5 were used. FIG. 1 shows the adsorption isotherm of PSSNa on the iron oxide crystals.

The uncoated iron oxide particles had a size of 130±5 nm as measured by PCS. Using a particle density of 5.2 g/l one can estimate the surface area of the particles as surface area $(m^2/ml) = m.A/\rho.V$ where m is the mass of particles per ml, ρ is the density of particles and A and V are the area and volume of a single particle respectively. The estimated surface area in the suspension was found to be $9.5 \times 10^{-1}$ $m^2/ml$ The maximum adsorbed amount then represents as much as 26 $mg/m^2$ indicating the build-up of multiple layers of adsorbed polymer or trains/loops of polymer extending from the surface.

Figure 2:
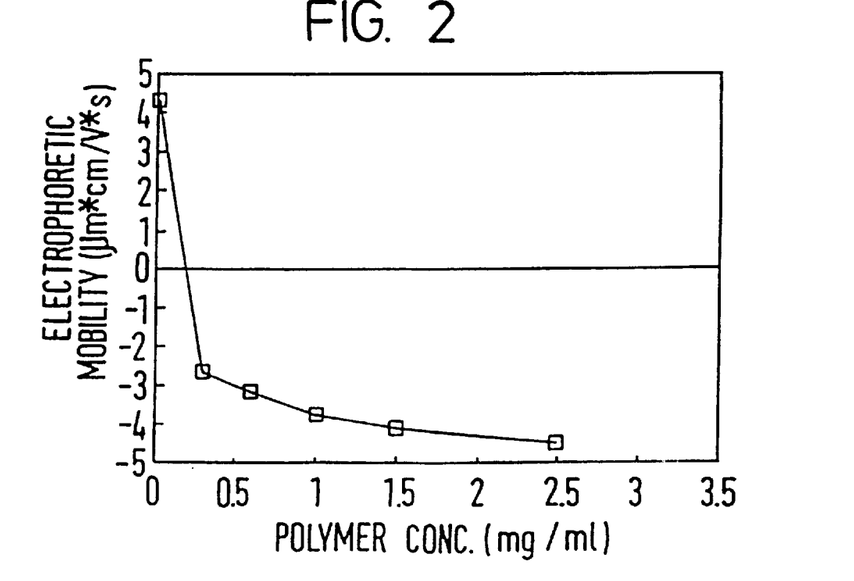
FIG. 2 is a graph which shows the electrophoretic mobility of colloidal iron oxide versus polymer concentration.
Figure 3:
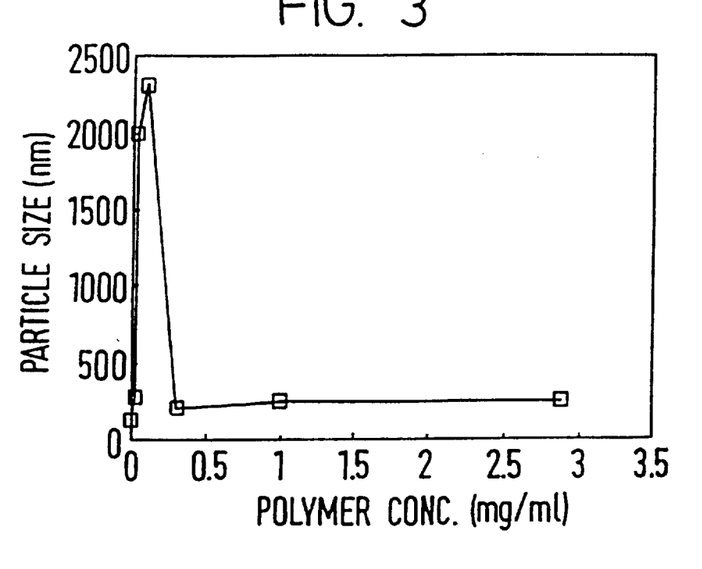
FIG. 3 is a graph which shows the particle size of colloidal iron oxide versus polymer concentration.

FIGS. 2 and 3 shows the electrophoretic mobility (E) of the particles and their hydrodynamic diameter as a function of polymer concentration. The electrophoretic mobility was found to be 4.2±0.6 µm·cm/V.s for the uncoated iron oxide particle and decreased rapidly with increasing polymer concentration. At high polymer concentration the electrophoretic mobility levels out around −4 µm·cm/V·s and the particle size seems to stabilize at 230±20 nm as measured by PCS. The results in FIGS. 1–3 are explained schematically in Table 1 below.

Figure 4:
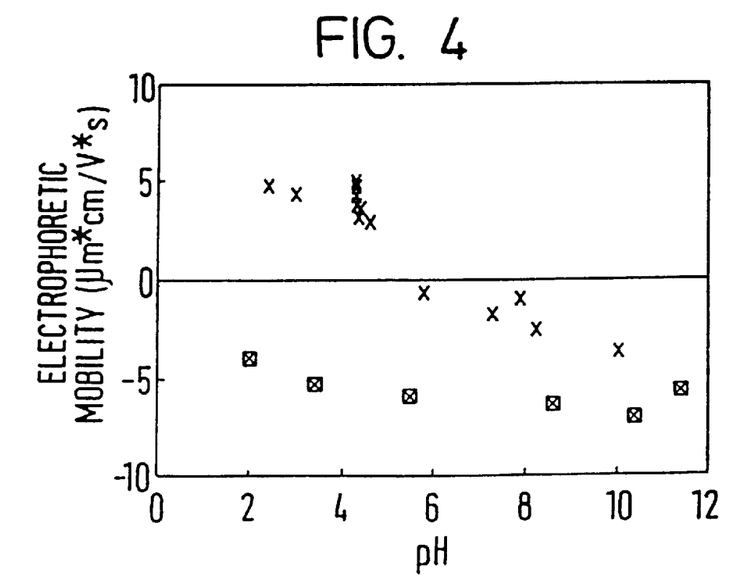
FIG. 4 is a graph which shows the electrophoretic mobility of pure colloidal iron oxide and coated colloidal iron oxide versus pH.

The results from the measurements of the electrophoretic mobility of uncoated as well as PSSNa coated iron oxide versus the suspension pH is shown in FIG. 4. The uncoated iron oxide surface displays a typically amphoteric nature going from the high positive electrophoretic mobilities at low pH to increasingly negative values with higher pH. The isoelectric point is located around pH 7. The characteristics of the particle surface are completely changed to display a persistently acidic nature when coated with PSSNa. This surface displays high negative electrophoretic mobilities even at low pH, changing slightly to a somewhat more negative surface at high pH. The results in FIG. 4 are consistent with FIGS. 1 to 3 showing evidence of a complete coverage of the original oxide surface with acidic polymer molecules at this polymer concentration.

Table 1: Effect of various PSSNa concentration on colloidal iron oxide suspension

| Polymer Concentration | Observations |
| --- | --- |
| Up to 0.01 mg/ml | High pos. mobility, stable suspension 0–0.5 mg polymer/$m^2$ |
| 0.03 up to 0.10 mg/ml | Mobility close to zero, unstable suspension, 1–5 mg polymer/$m^2$ |
| Above 0.3 mg/ml | High neg. mobility, stable suspension 10–20 mg polymer/$m^2$ |

FIG. 1: The absorbtion of PSSNa on colloidal iron oxide. Absorbed amount (mg/ml) versus concentration of PSSNa (mg/ml). ■ and ♦ is fraction by centrifugation, ▲ is fractionation by filtration.

FIG. 2: The electrophoretic mobility (µm·cm/V·s) of colloidal iron oxide versus concentration of PSSNa (mg/ml).

FIG. 3: The particle size of (nm) of colloidal iron oxide versus concentraion of PSSNa (mg/ml).

FIG. 4: The electrophoretic mobility (µm·cm/V·s) of pure colloidal iron oxide (x) and PSSNa coated colloidal iron oxide (x) versus pH.

Example 33

Figure 5:
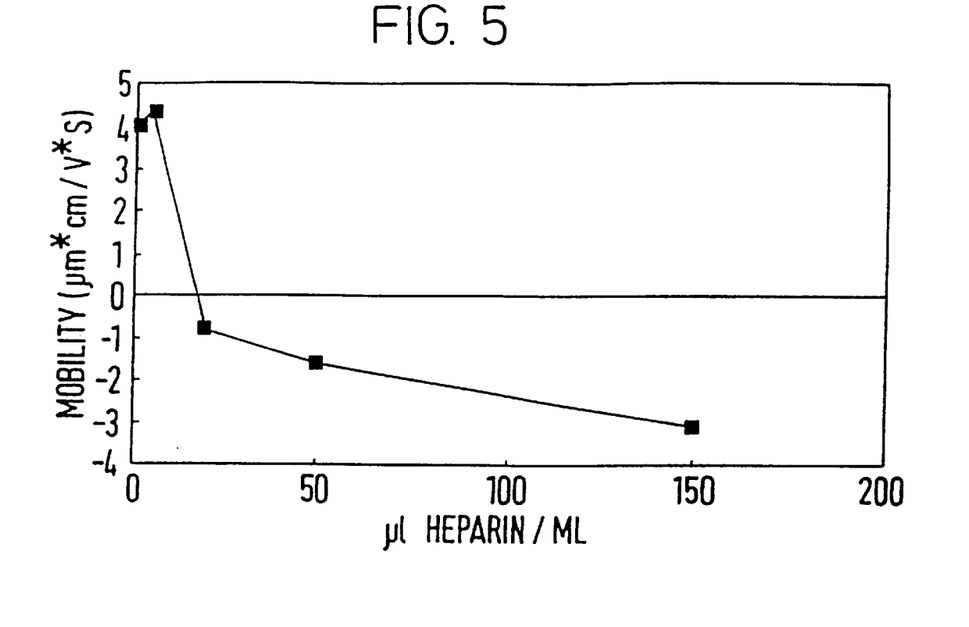
FIG. 5 is a graph which shows the electrophoretic mobility versus added heparin concentration.
Figure 6:
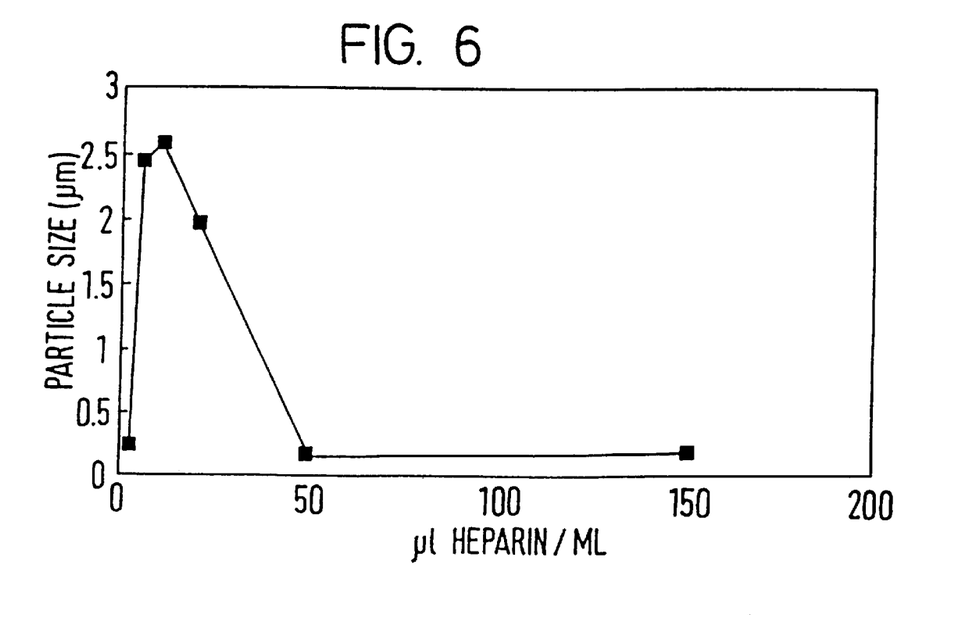
FIG. 6 is a graph which shows particle size versus added heparin concentration.

The adsorption of the typical polyelectrolyte polymer heparin to an iron oxide particle was studied. The electrophoretic mobility and particle size of the iron oxide particle was measured as a function of the heparin concentration. Bare particles from Example 1a, stabilized with HCl, were coated with heparin as described in Example 1b, however the dispersions were whirl mixed for 30 seconds instead of being sonicated. FIGS. 5 and 6 show the electrophoretic mobility and particle size versus heparin concentration.

The electrophoretic mobility and particle size profiles versus the amount of heparin show adsorption of the polymer to the particle surf ace. Increasing amounts of the negatively charged molecule on the positive iron oxide surface initially reduces and then reverses the electrophoretic mobility. The suspension is destabilized close to the isoelectric point.

FIG. 5: Electrophoretic mobility ($\mu$m·cm/V·s) versus added heparin concentration ($\mu$l/ml).

FIG. 6: Particle size ($\mu$m) versus added heparin concentration ($\mu$l/ml).

Safety

Example 34

The iron oxide formulations from Reference Example 4 (starch iron oxide) and Example 1b (heparin iron oxide) were administered as intravenous rapid bolus injections to rabbits (n 4–5). Dosages of 1, 2.5, and 10 mg Fe/kg were injected and the mean systemic arterial pressure (SAP) and the mean pulmonary arterial pressure (PAP) were recorded up to 60 minutes after injection. The formulation from Reference Example 4 showed a dose-dependent effect on PAP. No changes were detected at 1 mg Fe/kg while a minor increase from 20±1 mm Hg to 23±1 mm Hg was recorded for 2.5 mg Fe/kg. The 10 mg Fe/kg dosage increased the mean PAP from 22±3 mm Hg to 33±6 mm Hg. The higher dosage also gave a moderate decrease of mean SAP from 129±10 mm Hg to 117±8 mm Hg. The maximum effects on PAP and SAP were recorded 3–4 minutes after injection and the responses were of short (up to 10 minutes) duration. The formulation from Example 1b had no effect on the recorded hemodynamic parameters.

Example 35

The iron oxide formulations from Reference Examples 1 (dextran iron oxide), 4 (starch iron oxide), 5b (carboxy dextran iron oxide), and 6b (dextran phosphate iron oxide) and Examples 1b (heparin iron oxide), 4 (chondroitin-4-sulphate iron oxide) and 25a (poly-L-lysine iron oxide) were administered intravenously to rats (n=2–3) at a dosage of 1 mg Fe/kg. The number of circulating platelets was recorded 3, 5, 10, and 15 minutes after administration. The formulations from Reference Examples 1 and 4 caused a marked reduction in the number of platelets to 10–17% of pre-injection values at 3 and 5 minutes after injection. The formulation from Reference Examples 5b and 6b also gave significant reduction, similar to 50–60% of control, at 3 and 5 minutes. The response was rapidly recovered for all rats and platelet counts equal to 75–100% of control values were reattained within 15 minutes. The formulations from Examples 1b, 4 and 25a had no or only minor effect on the number of circulating platelets.

Example 36

The iron oxide formulations from Reference Examples 1 (dextran iron oxide), 4 (starch iron oxide), 5b (carboxy dextran iron oxide), and 6b (dextran phosphate iron oxide) and Examples 1b, 3a (heparin iron oxide), 4 (chondroitin-4-sulphate iron oxide), 11a (alginate iron oxide), 13a (chitosan iron oxide), 17a (poly-L-glutamate iron oxide) and 25a (poly-L-lysine iron oxide) were incubated with human serum in vitro in concentrations equivalent to dosages of 1 mg Fe/kg (all substances) and 10 mg Fe/kg (Reference Example 4 and 5b) for 60 minutes at 37° C. All formulations were sterilized by autoclaving and free of endotoxin. Enzyme immunoassay for the determination of human SC5b-a complement complex (TCC) (Bering) was used in order to study complement activation. Zymosan A (Sigma) was used as a positive control and dextrose (5%) or water as negative controls. The formulations in Reference Examples all significantly increased the TCC-levels. The effect was most marked for the sample in Reference Example Sb which gave 6-fold increase in TCC, even at the lower dosage of 1 mgFe/kg, when compared to the negative control. A dose-dependent effect on TCC was observed for the formulations in Reference Examples 1 and 4. The low dosages gave a 2-fold and the high dosages a 6-fold increase in the measured TCC-levels. The formulation from Reference Example 6b increased the TCC 3-fold at the low dosage of 1 mgFe/kg. The other tested formulations had no or only minor effects on TCC when compared with the negative control.

What is claimed is:

1. A diagnostic agent comprising a composite particulate material the particles whereof comprise a diagnostically effective, substantially water-insoluble, metal oxide crystalline material and a polyionic coating agent, wherein said particles have a size of below 300 nm, said crystalline material has a crystal size of from 1 to 100 nm, the weight ratio of said crystalline material to said coating agent is in the range 1000:1 to 11:1, and said coating agent is selected from the group consisting of natural and synthetic structural-type polysaccharides, synthetic polyaminoacids, physiologically tolerable synthetic polymers and derivatives thereof.

2. A diagnostic agent as claimed in claim 1 wherein said coating agent is a natural or synthetic structural-type polysaccharide selected from pectins, polygalacturonic acid, glycosaminoglycans, heparinoids, celluloses, and marine polysaccharides.

3. A diagnostic agent as claimed in claim 2 wherein said coating agent is selected from dermatans, heparins, heparans, keratans, hyaluronic acid, carrageenans and chitosans.

4. A diagnostic agent as claimed in claim 2 wherein said coating agent is a chondroitin.

5. A diagnostic agent as claimed in claim 1 wherein said coating agent is a homo or copolymer of aspartic acid, glutamic acid or lysine.

6. A diagnostic agent as claimed in claim 1 wherein said coating agent has a molecular weight in the range 500 to 2000000 D.

7. A diagnostic agent as claimed in claim 1 wherein the weight ratio of said metal oxide crystals to the surface bound coating agent is at least 15:1.

8. A diagnostic agent as claimed in claim 1 wherein the weight ratio of said metal oxide crystals to the surface bound coating agent is in the range 500:1 to 20:1.

9. A diagnostic agent as claimed in claim 1 wherein the weight ratio of said metal oxide crystals to the surface bound coating agent is in the range 100:1 to 25:1.

10. A diagnostic agent as claimed in claim 1 wherein said metal oxide crystals are superparamagnetic.

11. A diagnostic agent as claimed in claim 10 wherein said superparamagnetic crystals are iron oxide crystals.

12. A diagnostic agent as claimed in claim 1 wherein said particles exhibit a zeta potential which is less than −10 mV or greater than +10 mV.

13. A diagnostic composition comprising a diagnostic agent as claimed in claim 1 together with at least one physiologically tolerable carrier or excipient.

14. A process for the production of a diagnostic agent as claimed in claim 1, said process comprising:
(i) at a pH above 9, co-precipitating 1 to 100 nm crystals of a diagnostically effective substantially water-insoluble metal oxide and a coating agent or
(ii) coating 1 to 100 nm crystals of a diagnostically effective substantially water-insoluble metal oxide with a coating agent, whereby to yield a composite particle having a size below 300 nm and a crystal to surface bound coating agent weight ratio of 1000:1 to 11:1, said coating agent being selected from the group consisting of natural and synthetic structural-type polysaccharides and derivatives thereof, synthetic polyaminoacids and physiologically tolerable synthetic polymers.

15. A method of generating a contrast enhanced image of a human or non-human body, said method comprising administering to said body a suspension of a contrast agent as claimed in claim 1, generating an image of at least a part of said body into which said agent distributes.

* * * * *